US005709469A

United States Patent [19]

White et al.

[11] Patent Number: 5,709,469

[45] Date of Patent: Jan. 20, 1998

[54] PROCESS FOR TESTING INTEGRITY OF BONDS BETWEEN EPOXY PATCHES AND AIRCRAFT STRUCTURAL MATERIALS

[75] Inventors: William F. White; William H. Schueinberg, both of Warner Robins; Roy T. Mullis, Perry; James D. Armstrong, Warner Robins, all of Ga.

[73] Assignee: The United States of America as represented by the Secretary of the Air Force, Washington, D.C.

[21] Appl. No.: 748,733

[22] Filed: Nov. 18, 1996

Related U.S. Application Data

[63] Continuation-in-part of Ser. No. 402,745, Mar. 13, 1995, abandoned.

[51] Int. Cl.[6] .......................... G01N 25/72; G01N 25/00

[52] U.S. Cl. ............................... 374/5; 374/124; 228/104

[58] Field of Search .................................. 374/4, 5, 124; 228/103, 104

[56] References Cited

U.S. PATENT DOCUMENTS

| | | | |
|---|---|---|---|
| 5,032,727 | 7/1991 | Cox, Jr. et al. | 374/5 |
| 5,246,291 | 9/1993 | Lebeau et al. | 374/5 |
| 5,582,485 | 12/1996 | Lesniak | 374/5 |

FOREIGN PATENT DOCUMENTS

| | | | |
|---|---|---|---|
| 0565239 | 7/1977 | U.S.S.R. | 374/5 |
| 1198423 | 12/1985 | U.S.S.R. | 374/5 |
| 2168494 | 6/1986 | United Kingdom | 374/5 |

OTHER PUBLICATIONS

Schumacher, D., "Measuring Microbond Integrity with an Infrared Microradiometer," Materials Evaluation, pp. 257–260 (Dec. 1968).

Green, D, "Thermal and Infrared Nondestructive Testing of Composites and Ceramics," Materials Evaluation, vol. 29, No. 11, pp. 241–247 (Nov. 1971).

McLaughlin, P.V. et al., "Non–destructive examination of fibre composite structures by thermal field techniques," NDT International, pp. 56–62 (Apr. 1980).

W.P. Winfree, B.S. Crews, H.I. Syed, P.H. James and K.E. Cramer, "Thermographic Detection of Disbonds in Rivetted Lap Joints", Proceedings of the 37th International Instrumentation Symposium, pp.1097–1105, 1991.

W.P. Winfree, B.S. Crews and P.A. Howell, "Comparison of Heating Protocols for Detection of Disbonds in Lap Joints", Review of Progress in Quantitative Nondestructive Evaluation, edited by D.O. Thompson and D.E. Chimenti, vol. 11A, pp. 471–478, 1992.

H.I. Syed, W.P. Winfree, K.E. Cramer and P.A. Howell, "Thermographic detection of Corrosion in Aircraft Skin," Review of Progress in Quantitative Nondestructive Evaluation, edited by D.O. Thompson and D.E. Chimenti, vol. 12B, pp. 2035–2041, 1993.

H.I.Syed, W.P. Winfree and K.E. Cramer, "Processing Infrared Images of Aircraft Lapjoints," Thermosense XIV: An International Conference on Thermal Sensing and Imaging Diagnostic Applications, pp. 171–177, 1992.

(List continued on next page.)

*Primary Examiner*—Diego F.F. Gutierrez
*Attorney, Agent, or Firm*—William G. Auton

[57] ABSTRACT

A mechanical testing process for insuring composite patch bond integrity. A composite patch is applied to an aircraft aluminum skin. A thermal imaging system views the composite patch using both low and high heat techniques with prior calibration to a calibration standard. The inspection using these techniques produces images which are stored and these images so produced will display defects such as delaminations and disbonds, for example. These images are compared to calibration standard images to determine if the defect in the installed composite patch is sufficiently serious to require removal of the defective composite patch and another composite patch to be applied. Mechanical testing results are used in conjunction with thermography testing to determine composite patch bond integrity.

17 Claims, 1 Drawing Sheet

OTHER PUBLICATIONS

K.E. Cramer, H.I. Syed and W.P. Winfree, "Thermographic Detection of Cracks in Thin Sheets," Review of Progress in Quantitative Nondestructive Evaluation, edited by D.O. Thompson and D.E. Chimenti, vol. 10A, pp. 1087–1094, 1991.

K.E. Cramer, W.P. Winfree, E.R. Generazio, R.H. Bhatt and D.S. Fox, "The Application of Thermal Diffusivity Imaging to SIC–Fiber–Reinforced Silicon Nitride," Review of Progress in Quantitative Nondestructive Evaluation, ed. by D.O. Thompson and D.E. Chimenti, vol. 12B, pp. 1305–1311, 1993.

Winfree, W. et al., "Thermographic Detection of Disbonds," NASA Langley Research Center, MS 231, Hampton, VA (No Date).

W. N. Reynolds et al, "Application of thermal pulses and infrared thermal imagers for observing sub–surface structures in metals and composites", SPIE vol. 590 Infrared Tech. and Applications (1985)/293, pp. E–3—E8.

W. N. Reynolds et al, "The Non–Destructive Evaluation of Composites and Other Materials by thermal Pulse Video Thermography", SPIE vol. 520 Thermosense VII (1984) pp. T–15—T18.

Buchanan, Robert A. et al, "Recent advances in digital thermography for nondestructive evaluation", SPIE vol. 1313 Thermosense XII (1990) pp. T–67—T–75.

Bales, Maurice J. et al , "Pulsed Infrared Imaging: A New NDT Methodology for Aboveground Storage Tanks", Materials Evaluation/Jul. 1994, pp. 814–815.

Draft quality control specification dated Nov. 16, 1993.

PROCESS FOR TESTING INTEGRITY OF BONDS BETWEEN EPOXY PATCHES AND AIRCRAFT STRUCTURAL MATERIALS

CROSS REFERENCE TO RELATED APPLICATION

This application is a continuation-in-part of application Ser. No. 08/402,745 filed on 13 Mar. 1995, now abandoned, the disclosure of which is incorporated herein by reference.

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to a process for repairing aircraft structures, and, more particularly, relates to repairing damaged aircraft surface, and, in greater particularity, relates to the quality of composite patches placed on aircraft surfaces. The repair of aircraft surfaces, in particular, aluminum surfaces is a constant problem because of damage thereto caused by debris on the runway, hailstones, accidents during maintenance, etc. The repair may consist of applying a composite patch to an aluminum surface.

In the past, the integrity of the repair was primarily a visual inspection to determine if there was debonding or delaminations or misalignment.

Thus, there exists a need for a comprehensive testing procedure to insure that a repair meets a predetermined standard and that the repair is of high integrity.

SUMMARY OF THE INVENTION

The present invention is a testing procedure developed to insure that composite patches applied to aircraft aluminum surfaces are of high acceptable quality. Metal aircraft surfaces of aluminum, for example, can occur in areas, for example, exposed to high temperatures, low temperatures, high vibrations, fuels, and debris.

In this process composite patches are prepared and cured in an autoclave environment. Test specimens are prepared and cured at the same time as the composite patches. The test specimens are tested under shear and flexural strength tests.

After the composite patches are applied according to predetermined procedures, the composite patch is subjected to thermographic testing wherein defects in the area would appear. The appearance of the defects are compared to previously stored calibration standard images and criteria is established whether to accept or reject the repair under test based upon these standards. This procedure insures a consistent high quality repair.

The operation of the invention is as follows: first, calibrating a thermography subprocess using a calibration standard; second, storing respective images of the test calibration standard using a low heat and a high heat technique; and third, inspect the actual repair using two high heat and two low heat techniques and comparing the image of the actual repair to the images of the test calibration standard.

Therefore, one object of the present invention is a testing procedure for insuring bond integrity of repair when composite patches are applied to aircraft surfaces.

Another object of the present invention is a testing procedure for insuring bond integrity of repair when composite patches are applied to aircraft surfaces wherein the composites contain boron and are applied to aluminum aircraft surfaces.

Another object of the present invention is a testing procedure which establishes testing criteria upon which a particular repair is judged as acceptable or not.

Another object of the present invention is a testing procedure which is easily applied in the field environment.

These and many other objects and advantages of the present invention will be readily apparent to one skilled in the pertinent art from the following detailed description of a preferred embodiment of the invention and the related drawings.

BRIEF DESCRIPTION OF THE DRAWINGS

The only FIGURE illustrates a typical patch configuration.

DESCRIPTION OF THE PREFERRED EMBODIMENT

Figure 1:
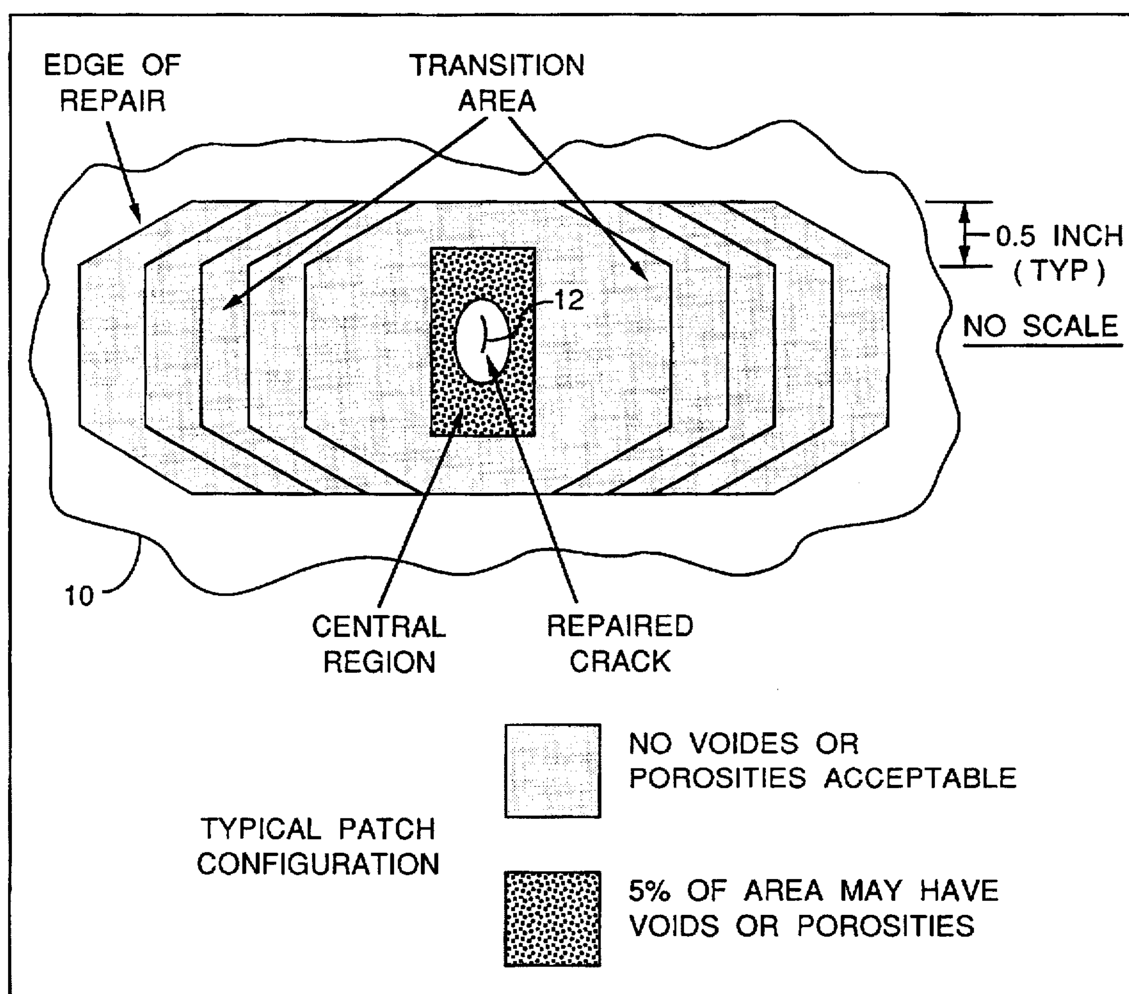

The FIGURE illustrates the repair of a small crack 12 in an aluminum skin 10 of an aircraft, not further detailed. In the FIGURE, the aircraft skin 10 is shown as being essentially flat. It is clearly possible to have skin damage in other locations on the aircraft wherein the skin is not flat such locations may be in a fuel tank, a wing panel, a belly panel, a vertical or horizontal control surface, a nose, etc. Each area may require its own testing standards because of conditions encountered as well as unique construction requirements of that area.

Each particular area may require modifications to the testing procedure, but the disclosed invention is acceptable in the testing of composite patches applied to aluminum skin having an essentially flat surface. Further, the testing procedure may require further modifications due to the testing environment wherein the environment is very cold or even very hot.

Preparation of Test Specimens:

This discussion refers to test specimens.

A test specimen is a composite patch whose installation is being tested. For precured composite patches, a minimum of one short beam shear test panel (minimum of three specimens) or one longitudinal flexural strength test specimens (minimum of three specimens) in one embodiment of the invention is prepared and cured with each lot of composite patches produced in an autoclave. For each cured composite patch, a minimum of one short beam shear rest specimen or one longitudinal flexural strength test specimen is produced and cured at the same time as the composite patch installation, using the same temperature and pressure as the composite patch. The test panels are prepared using the same materials and procedures as the composite patches, such that they are representative of the composite patches. The short beam shear test specimens shall be tested to the user's requirements, and the longitudinal flexural strength test specimen is tested to the requirements of the user. The minimum acceptable value for any one short beam shear test is 11,000 PSI, and the minimum acceptable average for the three specimens is 13,000 PSI. The minimum acceptable value of the longitudinal flexural strength test is 18,000 PSI.

Each precured composite patch shall be inspected using through transmission thermal imaging (thermography) or ultrasonics. Record inspection results (hard copy showing void location/orientation) and retain as part of permanent record of each precured composite patch.

Any voids or porosities shall be cause for rejection of a precured composite patch.

There shall be no delaminations in the precured composite patch.

There shall be no signs of resin starvation or resin pools (resin rich areas) except in the fiberglass topcoat.

No warping or off contour condition that cannot be removed with light vacuum (pressure≦10 in Hg) is acceptable.

Ply bias shall be within ±3 degrees of required and NO end to end butt joints in the material are acceptable (side by side or parallel to fiber direction are routine and acceptable).

A minimum of one adhesion test shall be used to insure proper adhesion of the installed composite patch. The adhesion test shall be in the form of a loading fixture bonded to the aircraft structure immediately adjacent to the composite patch. The area used for bonding the loading fixture shall have surface preparation accomplished in conjunction with preparation of surface for the composite patch. The loading fixture shall be cured in conjunction with the cure cycle of the composite patch. The same force shall be used on the loading fixture as on the composite patch during the cure cycle (i.e. same vacuum bag, mechanical force, etc.). The same heat source which is used to cure the composite patch shall be used when curing the loading fixture. The testing shall be accomplished in accordance with ASTM D4541-85, Standard Test Method for Pull-Off Strength of Coatings Using Portable Adhesion Testers. The minimum acceptable load required to pull a 0.5 inch diameter loading fixture (diameter of bonded area) is 3,416 pounds and 100% cohesive failure.

A visual inspection of the installed composite patch shall be performed to ensure the overall integrity of the composite patch and that adhesive flash is visible at the periphery of the repair. Any visual indication of poor quality in the installed composite patch, such as resin starved areas or inter laminar voids, or of incomplete bond, such as missing bondline adhesive flash shall be cause for rejection. There shall be visible signs of resin flash at all edges of the patch. There shall be no signs of structural fiber breakage. Results shall be recorded as a permanent record of the composite patch.

An inspection of the bondline shall be accomplished after installation of the composite patch on the aircraft. This inspection shall be accomplished using thermographic (thermal imaging) in accordance with the technique detailed herein.

Voids or porosity exceeding the following criteria shall be cause for rejection of the repair. Rejected composite patches shall be removed and replacement composite patches installed using extreme care to follow exactly the installation procedure. Additionally, a conductivity check shall be accomplished on the surrounding aluminum structure (wing panel) to verify that the bond cycle has had no detrimental effect on the temper (heat treat). The conductivity shall measure between 29.5% and 35% I.A.C.S.

Within one-half (0.5) inch of any edge of the repair, no detectable voids or porosities as defined herein are acceptable. Any void or porosity within this one-half inch zone shall be cause for removal and reinstallation of the composite patch.

Referring to FIG. 1, in the transition area which is defined as the area from the ends of the repair to where plies start "dropping off," nc detectable voids or porosities as defined herein are acceptable. Any void or porosity within this area shall be cause for removal and reinstallation of the repair. In the central area of the composite patch, defined as the region between the transition areas, up to 5% of the central area may be disbonded, with no one disbond greater than 0.5 inch in the longest direction with a total area not exceeding 0.050 square inches. If two or more disbonds are located within 0.5 inches of each other then they shall be considered a single disbond with a diameter equal to the sum of the diameters of the two disbonds plus the distance between the disbonds (measured on a straight line through the center points of the two disbonds). In the area within one inch of the repaired crack, no detectable voids or porosities as defined herein are acceptable. Any void or porosity within this area shall be cause for removal and reinstallation of the same composite patch.

The thermal inspection technique shall utilize a standard for calibration. The purpose of calibration is to assure that the technique can detect disbonds greater than a minimum size. The calibration standard utilized shall simulate a disbond with ¼ inch diameter in all ply configurations possible (1 ply up to a maximum number used on the composite patch). Thermographic images of the calibration standards shall be available on floppy disk detailing defects which should be discernable with properly performed integrity inspections. The inspection technique shall be used on the calibration standard immediately prior to each inspection and shall detect the simulated ¼ inch disbond.

The basic equipment used in conducting the integrity test is a thermal imaging system such as an Inframetrics Model 760 having video tape and floppy disk capabilities. A heat source such as a heat lamp. A ruler or tape measure for measuring distance between the heat source and the composite patch and a calibration standard, and predetermined criteria of an acceptable repair to that particular area.

The integrity testing procedure is initiated after each composite patch is applied. Testing personnel must receive formal equipment familiarization and procedure training prior to performing the thermography inspection procedure.

Calibration Sequence:

The calibration sequence shall be performed immediately prior to the first composite patch inspection and the calibration sequence shall be repeated following any change in inspection equipment, personnel, or ambient conditions within the same test period. The calibration sequence should be performed in the same ambient conditions as the actual inspections will be performed. The thermal imager is calibrated in the calibration sequence in the manner discussed below.

The thermal imager is powered up and allowed to stabilize. A video tape and disk are installed in the imager. The control settings are adjusted appropriately. The imager is, normally, aimed at the calibration standard at a distance of about three feet, but this distance should be the distance from the imager to the installed composite patch to be tested. The aiming angle between the calibration standard and the detector of the imager should not vary more than 45 degrees. The view is adjusted so that the calibration standard image will fill the monitor when viewing the calibration standard. The calibration sequence is recorded by video and stored.

The calibration sequence consists of two separate procedures: Low Heat and High Heat. The low heat technique is primarily for detection of delaminations and voids within the patch. The high heat technique is for detection of deeper defects, primarily disbonds or voids at the patch to aircraft surface bondline.

Low Heat Technique:

Heat Input Optimization Step

Set Temperature Span to 10 degrees Celsius. Set system to Point Mode and Place cursor in the center of the calibration standard. Note center spot Temperature on the monitor. This represents the calibration standard ambient temperature. Adjust Center Temperature to the approximate center spot Temperature. Apply light, uniform heat to the entire calibration standard surface by waving the heat lamp back and forth across the patch surface, then remove heat source. Monitor the center spot Temperature as it stabilizes immediately following heat removal. Adjust heat application technique as necessary (ie. distance between heat source and calibration standard, heating time, etc.) such that the center spot Temperature stabilizes between 3 to 5 degrees Fahrenheit above the initial calibration standard ambient temperature reading immediately following heat source removal.

If the heat is applied correctly, the calibration standard should cool at a uniform rate (in defect flee areas), resulting in a uniform gray scale on the system monitor which decreases in density as the calibration standard cools.

Inspection in the low heat mode:

When low heating technique is properly adjusted, one sets the system imager to Image Mode, Temperature Span to 2 degrees Celcius and adjusts the Center Temperature as required to obtain calibration standard image. Allow calibration standard to cool 2 minutes prior to inspection.

Using the technique established during the heat optimization step, apply uniform heat to entire calibration standard surface. Remove heat source and view the system monitor. Adjust the Center Temperature during cool-down as necessary to obtain the most detailed image. Note the image of ply steps, see FIG. 1, in the transition area of the calibration standard. The steps should be visible almost immediately following heat removal. From calibration standard to calibration standard, the number of steps visually resolvable varies. On some calibration standards no ply steps will be noted. As the calibration standard cools any step images visible will fade and become unresolvable. Any near surface defects such as ply delaminations should also be visible almost immediately following heat removal. Delaminations act as a heat sink and will create a distinctive heat pattern on the patch image. Delamination images will have a longer decay time than the defect free portions of the calibration standard. Dependent on defect severity, some deeper defect images may also appear during the low heat technique. The image obtained should be similar to the previously stored disk image for the calibration standard used. This image may be read from a previously stored disk.

High heat technique:

Heat input optimization step:

One allows the calibration standard to cool a minimum of 2 minutes from the low heat technique. Sets the Temperature Span to 10 degrees Celcius. Sets the imager to Point Mode and places cursor in the center of the calibration standard. Notes the center spot Temperature on the monitor. This represents the calibration standard ambient temperature before heat application. Adjusts the Center Temperature to the approximate center spot Temperature. Applies uniform heat to the entire calibration standard surface (heavier than the previous step) and then removes the heat source. Monitors the center spot Temperature as it stabilizes immediately following heat removal. Adjust the heat application technique as necessary such that the center spot Temperature stabilizes between 7 and 10 degrees Fahrenheit above the initial calibration standard ambient temperature reading immediately following heat source removal. To determine if the heat was applied correctly, a check of the calibration standard temperature should be taken immediately following the heat source removal. If the heat was applied correctly, the calibration standard should cool at a uniform rate in defect free areas resulting in a uniform gray scale which decreases in density as the calibration standard cools.

Inspection in high heat mode:

When high heating technique is properly adjusted one sets the imager to Image Mode, Temperature Span to 2 degrees Celcius, and adjusts the Center Temperature as required to obtain calibration standard images. Allows the calibration standard to cool 2 minutes prior to inspection. Using the technique established during the high heat optimization step, apply uniform heat to the entire calibration surface. Remove the heat source and view the system monitor and adjust the Center Temperature during cool-down as necessary to obtain the most detailed image. One notes the image of the ply steps in the transition area of the calibration standard. If steps were not resolvable during low heat inspection they will not be visible with the high heat technique. Following a short cool down period an image caused by a riser (aircraft panel substructure) (a cool spot) should start appearing in the center of the calibration standard along the entire length of the patch. The riser image will be faint but should be discernible for several seconds. The high heat and low heat optimization steps are used on the calibration standard during the calibration sequence, and on the installed composite patch as described above.

Any bondline defects such as disbonds should also begin to appear following a short cool-down period. Disbonds creates a distinctive heat pattern on the calibration standard surface. Due to depth, disbonds require more heat input for detection than near surface defects. Disbonds and other deep defect images tend to have longer image decay times than near surface defect images.

The image obtained should be similar to the previously stored disk image for the calibration standard in use. This image may be read from a previously stored disk.

Extreme ambient conditions such as cold or wind may require deviation from the specified heat input limitations. If so, adjust the heat input calibration until the thermal images closely match the previously stored images of the calibration standards. When final adjustments have been made one can proceed to the inspection sequence as follows for an installed composite patch.

Inspection for installed patch composite integrity:

Preinspection: Remove any protective covering on the composite patch. Visually inspect the composite patch surface. An adhesive flash should be visible around the entire periphery of the composite patch. Note the location of any area where adhesive flash is not visible and the location of any visual surface anomolies which may give an indication during thermography inspection. Further, note any aircraft structure locations in relation to the composite patch. Note the location of fasteners if the composite patch is located on a lap joint. The imager settings are input as required. For example, one selects the image or point mode, black and white mode, and temperature span of 2 degrees Celsius with black equal to hot. The imager average mode is set at 16 frames per second, target emissivity of 1.0, background temperature as necessary, filter/temperature range of open and normal and external optics trains of 1.0.

Detector aiming and heat input optimization controls are the same as specified during the calibration sequence described above.

When proper heat input techniques are developed, perform two (2) Low Heat Technique and two (2) High Heat Technique Inspections, respectively on the installed composite patch. Allow 2 minute cool down period between all inspections.

Record a minimum of one entire inspection sequence for each technique.

The inspection sequence includes heat application and a minimum of thirty seconds cool down following heat source removal. Each inspecting sequence consists of the application of the two high heat and the two low heat techniques to the actual repair.

Adjust the Center Temperature manually as required to maintain the best image on screen while recording.

If any indications occur (any deviation from uniform background) reinspect and determine if the same indication pattern reappears. Allow a minimum 2 minute cool down period prior to all reinspections.

Record a minimum of one reinspection sequence using Manual Center Temperature adjustment during cool down. Record a minimum of one reinspection in the Point Mode using Auto Center Temperature adjustment (No Manual Adjustment). All reinspections shall be recorded until indications are no longer visible on the monitor.

During reinspection save an image to the floppy disk which best displays the indications of interest. Prior to storing the image to disk change to the Color Mode and select Color Palette #8. After storing the image, change back to B & W Mode. NOTE: After storing image #25, replace the disk.

Patch Inspection Acceptance Criteria

Acceptance or rejection of the patch bond integrity shall be based on the criteria specified herein.

Reporting and Archiving Requirements

All recorded inspection images shall be identified with the A/C Serial No., composite patch ID and location.

The recorded data for all installed composite patches shall be archived and kept as a permanent record of the repair.

Integrity Criteria:

Verify that the recommended "out times" and temperatures for all materials requiring refrigeration has not been exceeded. Keep written records to document out times of adhesive, prepregs and primer.

A check list verifying the steps in application of the composite patch shall be developed and used to ensure each step in the repair is completed. This list shall be used to certify that each required step in the repair procedure is satisfactorily completed and at the completion of the repair, the list will be signed-off by the certified repair technician and witnessed by a second certified individual. This will become a part of the permanent repair record.

Records of applied pressure and temperature to the composite patch during cure shall be made and kept as a permanent record of the repair.

Clearly, many modifications and variations of the present invention are possible in light of the above teachings and it is therefore understood, that within the inventive scope of the inventive concept, the invention may be practiced otherwise than specifically claimed.

What is claimed is:

1. A process for insuring the integrity of a composite patch applied to an aircraft surface, said process comprising the steps of:

a) training of test personnel on test equipment and on bond integrity test procedures;

b) preparing and installing said composite patch for mechanical testing purposes;

c) visually inspecting said composite patch that has been installed on an essentially flat surface to determine visible defects and location of said composite patch within an aircraft structure;

d) selecting a thermographic calibration standard with previously stored thermograhpic images of defects obtained using a low heat process and a high heat process;

e) calibrating a thermographic subprocess to get a calibrated thermographic subprocess using said thermographic calibration standard and by optimizing the low heat and high heat processes said calibrating thermographic subprocess including the use of a calibrated thermographic imager;

f) performing two low heat processes on said installed composite patch;

g) inspecting said installed composite patch using said calibrated thermographic subprocess and recording an image of said composite patch after said two low heat processes have been performed;

h) comparing said image of said composite patch obtained using said two low heat processes to an image of defects of said thermographic calibration standard obtained with the low heat process;

i) allowing said installed composite patch to cool down for a predetermined period of time;

j) performing two high heat process on said installed composite patch;

k) inspecting said installed composite patch using said calibrated thermographic subprocess and recording an image of said composite patch after said two high heat processes have been performed;

l) comparing said image of said composite patch obtained using said two high heat processes to an image of defects of said termographic calibration standard obtained with the high heat process;

m) recording said images of said composite patch in said calibrated thermographic imager during each inspecting step to obtain recordings;

n) reinspecting said composite patch by repeating the performing the two low heat process steps, the inspecting with said two low heat processes step, the comparing the image using said two low heat processes step, the allowing of the composite patch to cool down step the performing the two high heat processes step, the inspecting with said two high heat processes step, the comparing the image using said two high heat processes step, and the recording step if during said recording in said image of said images said defect is seen therein, said reinspecting including recording the reinspecting images of said composite patch in said imager;

o) determining whether said installed composite patch meets predetermined criteria which will insure the integrity of the composite patch being applied to the aircraft surface by analyzing the reinspected images;

p) identifying said installed composite patch being tested; and q) archiving said recordings for future reference.

2. A process as defined in claim 1 wherein said composite patch is a boron composite patch.

3. A process as defined in claim 1 wherein said aircraft surface is made of metal and said metal is aluminum.

4. A process as defined in claim 1 wherein said thermographic calibration standard is a bonded composite patch, and said defects include simulated ¼ inch diameter defects in all ply configurations.

5. A process as defined in claim 1 wherein said defects obtained with said low heat process comprises delaminations.

6. A process as defined in claim 1 wherein said defects obtained with said high heat process comprises disbonds and porosity at said composite patch to aircraft surface bondline.

7. A process as defined in claim 1 wherein said low heat process comprises applying a heat source to a composite patch surface such that the surface temperature is raised 3 to 5 degrees Fahrenheit above an ambient temperature.

8. A process as defined in claim 1 wherein said high heat process comprises applying a heat source to a composite patch surface such that the surface temperature is raised 7 to 10 degrees Fahrenheit above an ambient temperature.

9. A process as defined in claim 1 wherein said training includes training of the use of a check list for verifying each step.

10. A process as defined in claim 1 wherein said preparing and installing step includes a mechanical subprocess wherein said composite patch is tested for short beam shear and flexural strength.

11. A process as defined in claim 10 wherein in said mechanical subprocess a minimum acceptable value of said short beam shear test is 11,000 PSI and wherein a minimum acceptable value of said flexural strength test is 18,000 PSI.

12. A process as defined in claim 10 wherein in said mechanical subprocess a minimum acceptable load required to pull a 0.5 inch diameter loading fixture is 3,416 pounds with 100% cohesive failure.

13. A process as defined in claim 1 wherein in said inspecting step after said two low heat processes have been performed, said composite patch is unacceptable if the defects include any voids, porosities, delaminations, resin starvation or resin pools therein.

14. A process as defined in claim 1 wherein said predetermined criteria includes a conductivity check on a surrounding aluminum structure that surrounds the composite patch, to test for changes in heat treatment values.

15. A process as defined in claim 1 in which said predetermined criteria requires that there be no defects in a transition area of said composite patch.

16. A process as defined in claim 1 in which said predetermined criteria requires that the defect be no more than 5% of a central area of the composite patch may be disbonded with no one disbond greater than 0.5 inches in a longest direction with a total area not exceeding 0.050 square inches.

17. A process as defined in claim 1 in which said predetermined criteria requires that there be no detectable defects within one inch of a repaired crack.

* * * * *